United States Patent
Görl et al.

(10) Patent No.: US 6,194,594 B1
(45) Date of Patent: *Feb. 27, 2001

(54) MIXTURE OF ORGANOSILANEPOLYSULPHANES AND A PROCESS FOR THE PRODUCTION OF RUBBER COMPOUNDS CONTAINING THESE MIXTURES

(75) Inventors: Udo Görl, Bornheim; Horst Lambertz, Hürth, both of (DE)

(73) Assignee: Degussa-Huls AG, Frankfurt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/889,136

(22) Filed: Jul. 7, 1997

(30) Foreign Application Priority Data

Jul. 18, 1996 (DE) .............................................. 196 28 904
Jan. 22, 1997 (DE) .............................................. 197 020 46

(51) Int. Cl.$^7$ ..................................................... C08F 7/18
(52) U.S. Cl. ......................... 556/427; 524/493; 524/575; 524/575.5; 524/571
(58) Field of Search ............................. 556/427; 524/493, 524/575, 575.5, 571

(56) References Cited

U.S. PATENT DOCUMENTS

| | | | |
|---|---|---|---|
| 3,873,489 | * 3/1975 | Thurn et al. ................. | 260/33.6 AQ |
| 4,595,740 | 6/1986 | Panster et al. ................. | 528/30 |
| 5,405,985 | 4/1995 | Parker et al. ................. | 556/427 |
| 5,468,893 | 11/1995 | Parker et al. ................. | 556/427 |
| 5,580,919 | * 12/1996 | Agostini et al. ................. | 524/430 |
| 5,596,116 | 1/1997 | Childress et al. ................. | 556/427 |
| 5,663,395 | 9/1997 | Gobel et al. ................. | 556/427 |
| 5,663,396 | * 9/1997 | Musleve et al. ................. | 556/427 |
| 5,674,932 | * 10/1997 | Agostini et al. ................. | 524/430 |
| 5,684,171 | * 11/1997 | Wideman et al. ................. | 556/427 |
| 5,684,172 | * 11/1997 | Wideman et al. ................. | 556/427 |

* cited by examiner

Primary Examiner—Margaret G. Moore
(74) Attorney, Agent, or Firm—Pillsbury Madison & Sutro LLP

(57) ABSTRACT

This invention relates to mixtures of organosilane-polysulphanes of the general formula $$(RO)_3Si(CH_2)_xS-S_z-S(CH_2)_xSi(OR)_3 \quad (I)$$

in which

R means alkyl, linear or branched, having 1–8 C atoms, in particular 1–3 C atoms x means an integer from 1–8 z means 0 to 6, wherein sum of the proportions of polysulphanes in which z=0 and z=1 amounts to ≧80% by weight, providing that the proportion of compounds in which z=0 remains below 80% and the proportion of organosilanepolysulphanes in which z means an integer from 2 to 6 does not exceed a proportion of 20 wt. % in the mixtures, and to the rubber compounds produced using these mixtures, in particular for tire treads.

13 Claims, 3 Drawing Sheets

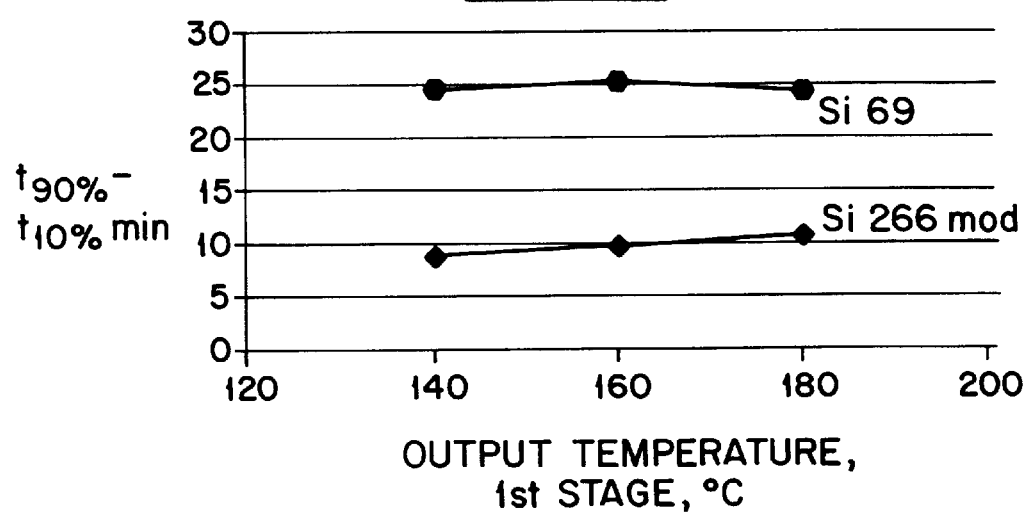
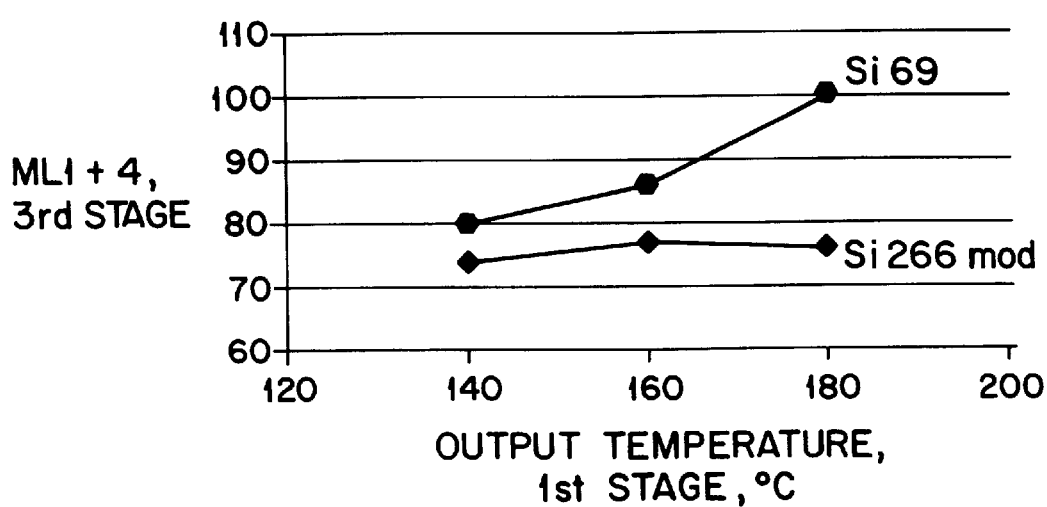

MIXTURE OF ORGANOSILANEPOLYSULPHANES AND A PROCESS FOR THE PRODUCTION OF RUBBER COMPOUNDS CONTAINING THESE MIXTURES

CROSS-REFERENCE TO RELATED APPLICATIONS

This application claims priority from German applications 19628904.1, filed Jul. 18, 1996, and 19702046.1, filed Jan. 22, 1997, the subject matter of which is hereby incorporated herein by reference.

BACKGROUND OF THE INVENTION

1. Field of the Invention

This invention relates to mixtures of organosilanepolysulphanes having an elevated proportion of disulphanes and to a process for the production of rubber compounds containing these compounds.

2. Prior Art

Due to increasing environmental awareness, economies in fuel consumption and a reduction in pollutant emissions are today becoming a greater priority [Auto 91/92, Verband der Autombobilindustrie e.V., Frankfurt, ADAC-Motorwelt 11791, 50 (1991]. The challenge to tire manufacturers is to develop tires which are distinguished by very low rolling resistance combined with excellent wet skid resistance and good abrasion resistance.

Proposals have been made in numerous publications and patents with regard to reducing tire rolling resistance and thus fuel consumption. Proposals which may be mentioned include reducing the carbon black content in the compound and using special carbon blacks (U.S. Pat. No. 4,866,131, U.S. Pat. No. 4,894,420). However, none of these proposed solutions has resulted in a satisfactory balance between the desired low rolling resistance and other important tire characteristics such as wet skid resistance and abrasion resistance.

The use of highly active silica fillers in combination with organosilane bis(triethoxysilylpropyl)tetrasulphane (TESPT) to replace the carbon black normally used in rubber compounds is known to allow production of a tire having rolling resistance substantially reduced in comparison with standard tires, while simultaneously retaining or even improving the other two above-stated tire characteristics [EP 0 501 227, U.S. Pat. No. 5,227,425; G. Agostini, J. Berg, Th. Materne: New Compound Technology, October 1994, Akron, Ohio, USA; S. Wolff, U. Gorl, M. J. Wang, W. Wolff: Silica based on tread compounds—background & performance, paper presented at TYRE TECH '93, October 1993, Basel, Switzerland; Ph. Cochet, L. B. Barriquand: Precipitated silica in tire tread, paper presented at ACS Meeting of the Rubber Division, October 1995, Cleveland, Ohio, USA].

At the 1986 ACS meeting in New York S. Wolff [S. Wolff: The influence of fillers on rolling resistance, presented at the $129^{th}$ meeting of the Rubber Division, American Chemical Society, Apr. 8–11, 1986, New York] presented a paper showing that it is possible to reduce rolling resistance in comparison with a carbon black filled standard compound while largely retaining wet skid resistance by using silica in combination with TESPT both in a passenger vehicle tire tread based on an emulsion styrene/butadiene rubber (E-SBR) and in a truck tire tread based on natural rubber.

This system was further optimized with regard to all three characteristics by using specific styrene/butadiene polymers produced using a solution polymerization process (EP 0 447 066 A1), sometimes blended with other polymers, in particular polybutadiene and additionally using novel grades of silica (U.S. Pat. No. 5,227,425) and polymer blends specifically tailored to this application (EP 0 620 250 A1) sometimes with three to four different starting polymers [G. W. Marwede, U. G. Eisele, A. J. M. Sumner: paper presented to the ACS Meeting of the Rubber Division, October 1995, Cleveland, Ohio, USA.].

It is stated in all the publications and patents that, in order to achieve a lower rolling resistance while retaining or improving wet skid resistance and abrasion resistance, it is necessary to replace a large proportion of or the entire content of the normally used carbon black filler with a highly active silica [S. Wolff: The influence of fillers on rolling resistance, presented at the $129^{th}$ meeting of the Rubber Division, America Chemical Society, Apr. 8–11, 1986, New York; U. LeMaitre: Tire rolling resistance, AFCEP/DKG Meeting, 1993, Mulhouse, France]. However, this replacement results in the desired objective only if the organosilane bis(triethoxysilylpropyl)tetrasulphane (TESTP) is used as a "coupling" agent between the silica and the polymer.

It is known [S. Wolff: The role of rubber-to-silica bonds in reinforcement, presented at the First Franco-German Rubber Symposium, Nov. 14–16, 1985, Obernai, France; S. Wolff: Silanes in tire compounding after ten years—review, Third Annual Meeting & Conference on Tire Science & Technology, The Tire Society, Mar. 28–29, 1984, Akron, Ohio, USA] that the properties which may be achieved by using organosilanes in rubber compounds are dependent upon two independent reactions. Firstly, during production of the compound, preferably during the first compounding stage, a reaction occurs at elevated temperature between the silanol groups of the silica and the trialkoxysilyl groups of the silane with elimination of alcohol (hydrophobing or modification reaction). A complete reaction is of decisive significance to subsequent properties.

Like all chemical reactions, this reaction proceeds faster at elevated temperatures [U. Gorl, A. Hunsche: Advanced investigations into the silica/silane reaction system, paper presented at ACS Meeting, Rubber Division, October 1996, Louisville, Ky., USA], such that the rubber compounder, desiring short compounding times, prefers to use the highest possible compounding temperature. The use of such high compounding temperatures is, however, limited by the fact that the second, so-called rubber-reactive group of TESPT consists of a group which is on average a tetrasulphane group having a significant proportion of longer sulphane chains ($S_5$–$S_8$) [S. Wolff: Silanes in tire compounding after ten years—review, Third Annual Meeting & Conference on Tire Science & Technology, The Tire Society, Mar. 28–29, 1984, Akron, Ohio, USA].

This rubber-reactive group is generally considered to give rise to a so-called filler/rubber bond, which determines the technical rubber properties of the finished article (for example tires). This reaction, which is desired during vulcanization, is influenced by the thermal lability of the tetrasulphane group and higher sulphane units. Practical experience has, however, shown that the reaction causes serious problems if it occurs during production of the unvulcanised compound, during which only the reaction between the filler and the silane should normally occur.

If sulphur is eliminated from the long-chain sulphane units, it is incorporated into the polymer chain. This then brings about "scorching" and stiffening of the sheeted compound, which can even render the unvulcanized compound unprocessable. Scorching can be measured by determining the viscosity of the compound. EP-A1-0 732 362, which is not a prior publication, describes the use of organosilanedisulphides in rubber compounds.

However, these sulphur compounds must be very pure or have a disulphide content of at least 80%.

SUMMARY OF THE INVENTION

The object of the invention is to provide mixtures of organosilanepolysulphanes which do not give rise to scorching at the elevated temperatures which may occur during production of unvulcanized rubber compounds, i.e. vulcanizable rubber compounds, which still do not yet contain the sulphur and accelerator(s) necessary for vulcanization.

The present invention provides mixtures of polysulphanes which achieve this object.

The mixtures of the invention comprise organosilanepolysuphanes of the general formula

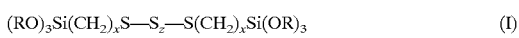

$$(RO)_3Si(CH_2)_xS-S_z-S(CH_2)_xSi(OR)_3 \quad (I)$$

in which

R is alkyl, linear or branched, having 1–8 carbon atoms, preferably 1–3 carbon atoms, x is an integer from 1–8, and z is 0 to 6, wherein the sum of the proportions of organosilanepolysulphanes in which z=0 and z=1 amounts to ≧80% by weight, providing that the proportion of compounds in which z=0 remains below 80% and the proportion of organosilanepolysulphanes in which z is an integer from 2 to 6 does not exceed 20 wt. % of the mixtures.

The latter should be stated as a content of ≦20% by weight and is a vital characterizing feature. Polysulphane fractions where z=7 or 8 are not generally found in the mixtures according to the invention. These polysulphane fractions can be present at contents of <1%, for example as impurities, which have no effect on the use of the mixtures according to the invention.

The sum of the constituents must, of course, always be 100%, if necessary taking account compounds where z is 7 or 8.

Particularly suitable mixtures are those in which the proportions of the organosilanepolysulphanes have the following values:

z=0 approx. 58 to <80 wt % z=1>0 to approx. 32 wt %, wherein the sum of these compounds is ≧80 wt %, and z=2 to 6≦20 wt %, preferably<11 wt %.

BRIEF DESCRIPTION OF THE DRAWINGS

FIGS. 2–5 graphically illustrate a comparison in vulcanized properties between a control (Si 69) and a product of the invention (Si 266 mod) in the specific examples.

DETAILED DESCRIPTION OF INVENTION

Figure 1:
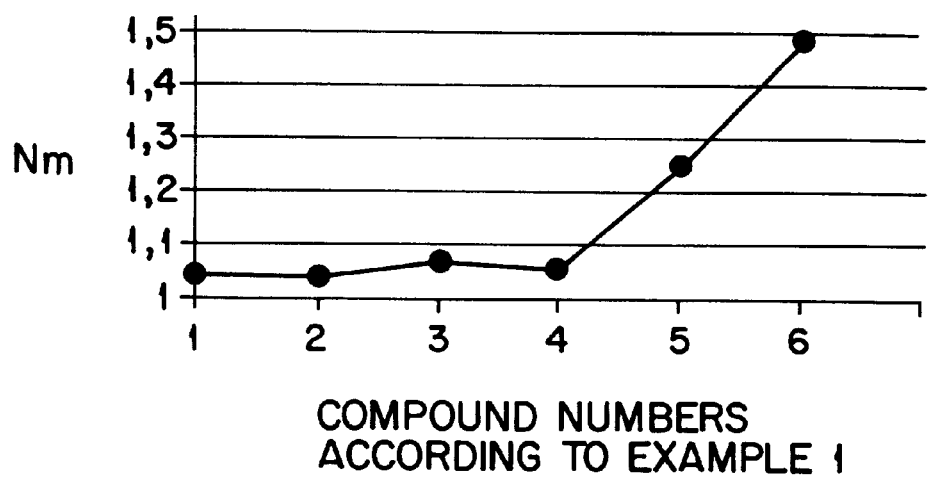
FIG. 1 illustrates graphically the scorching behavior of the unvulcanized compounds of Example 1.

The mixtures according to the invention are used in the production of vulcanizable rubber compounds, in particular for tires. The polymers used in these compounds are natural and synthetic elastomers, whether oil-extended or not, as individual polymers or blended with other rubbers, such as for example natural rubbers, butadiene rubbers, isoprene rubbers, butadiene/styrene rubbers, but in particular SBR, produced using a solution polymerization process or an emulsion process.

The term mixture should be taken to mean that it is possible on the one hand to produce compounds from a pure polysulphane of the formula (I) where x=0 and other polysulphanes, in which x≠0, but which comply with the definitions described herein.

On the other hand, it is, however, also possible by means of a suitable production process to obtain the mixtures according to the invention directly or by adding other polysulphanes.

The mixtures according to the invention are primarily used in tire tread compounds having an elevated silica content, such as are described, for example, in EP-A1-0 447 066 and EP-A-0 620 250.

Rubber compounds produced using the mixtures according to the invention are generally vulcanized with sulphur and/or sulphur donors and accelerators (vulcanization auxiliaries), wherein the quantity of sulphur is generally between 0.1 and 4 phr.

In addition to the polymers and the additives conventional in practice, such as activators, anti-oxidants, processing auxiliaries, the rubber compounds optionally contain carbon black and also natural, light-colored fillers, but in any case the rubber compounds contain highly active silica fillers in quantities of 10 to 200 parts, in particular 25 to 80 parts, relative to 100 parts of the polymer. These fillers are characterized in that they have BET surface areas of 1 to 700 $m^2/g$, preferably of 100 to 250 $m^2/g$, and also a DBP value of 150 to 300 ml/100 g.

Suitable forms for the components of the invention are not only powders, but also low-dusting forms such as pellets and microbeads. The quantity of the mixtures according to the invention is between 0.5 and 30 parts by weight, relative to 100 parts by weight of filler. In preferred applications, such as for example tire tread compounds having an elevated silica content, in which silicas of 100 to 250 $m^2/g$ are generally used, the mixtures according to the invention are used in quantities of between 4 and 10 weight parts, relative to 100 weight parts of the filler.

The mixtures according to the invention can be introduced into the compound in situ, or previously mixed with carbon black.

Premodification of the silica used as filler, as is described, for example, in DE 196 09619.7, is also possible.

Particular attention must be paid to the process for the production of highly silica filled compounds in combination with organosilanes. A suitable process is described in application EP 0 447 066 A1, wherein, due to the use of TESPT, it is, however, necessary in that process not to allow the temperature during compounding to exceed 160° C., so as not to initiate the above-mentioned scorching. However, when using the compounds according to the invention, temperatures of 160 to 200° C., in particular of 175 to 190° C. are possible without causing this disruptive effect to occur. The compounder may thus select higher temperatures and so accelerate the reaction between the silica and silane, i.e. reduce compounding time and/or the number of compounding stages. Compounding conditions are thus largely freely selectable.

The mixtures according to the invention can be used in virtually any rubber article. The inventive mixtures are particularly suitable for use in silica filled compounds (containing >40 weight parts of $SiO_2$, relative to 100 weight parts of rubber), in particular tire tread compounds, in which large quantities of silane must generally be used in order to achieve the required properties.

The stated rubber compounds, like the process for the production thereof, are provided by the present invention.

In actual practice, the process for the production of rubber compounds vulcanized with sulphur and/or sulphur donors and accelerator(s) and containing one or more natural or synthetic rubbers, light-colored oxide (silicate) fillers, optionally together with carbon black and further conventional constituents, is characterized in that the rubber component(s), the polysulphane mixtures according to the invention, the silicate filler and the optionally present carbon black, optionally together with a plastiziser, anti-oxidants and activators are kneaded for 3 to 15 minutes in a single stage or in multiple stages in a kneading apparatus, optionally a Banbury internal mixer, at a temperature of 160 to 200° C. preferably at 175 to 190°, then, either in the Banbury internal mixer or in a roll mill, vulcanization auxiliaries are added at 60 to 120° C., preferably at 80 to 110° C., compounding is continued for a further 2 to 10 minutes at the stated temperature range and the finished rubber compound is then rolled out into sheets or strips.

The present invention thus also relates to the use of organosilanepolysulphane mixtures, the sulphane chain distribution of which is selected in such a manner that even at temperatures of 160 to 200° C., in particular 175 to 190° C., there is no discernible scorching of the unvulcanized compound. In practice, this scorching may be evaluated from the properties of the unvulcanized sheet, which becomes increasingly rough and crumbly as scorching occurs and can often become unprocessable on the roll mill. In the laboratory, scorching can be identified by measuring the viscosity of the compound and by determining the minimum torque value of the unvulcanized compound in the rheometer test. A guide value for any increase in viscosity in comparison with a formulation compounded at a lower temperature (=more reliable processing behavior) of more than 5, in particular of more than 10 Mooney units can be set as an indication of scorching of the compound.

DETAILED DESCRIPTION OF THE PREFERRED EMBODIMENTS

FIG. 1 graphically illustrates the scorching behavior of the unvulcanized compounds of Example 1. The rheometer data is obtained at 165° C.

FIGS. 2–5 graphically illustrate a comparison in vulcanized properties between a control (Si 69) and a product of the invention (Si 266 mod) as used in the specific examples.

Figure 2:
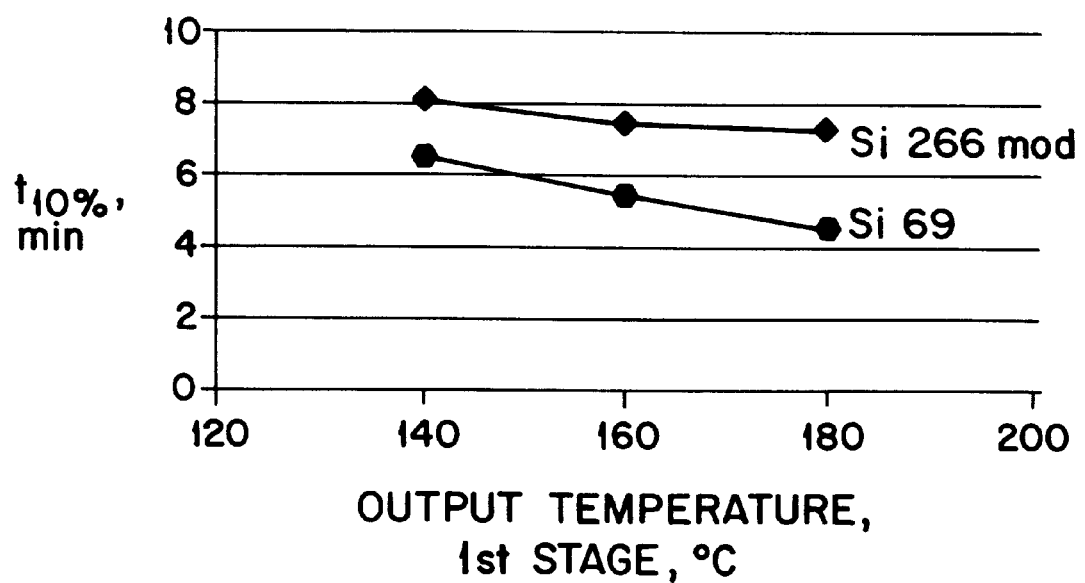

FIG. 2 shows that Si 266 mod exhibits distinctly improved scorching behavior at all compounding temperatures.

FIG. 3 shows that Si 266 mod exhibits a distinctly more favorable vulcanization time in comparison with Si 69.

FIG. 4 shows that even at elevated compounding temperatures, Si 266 mod exhibits no scorching and thus has distinctly better processing behavior.

Figure 5:
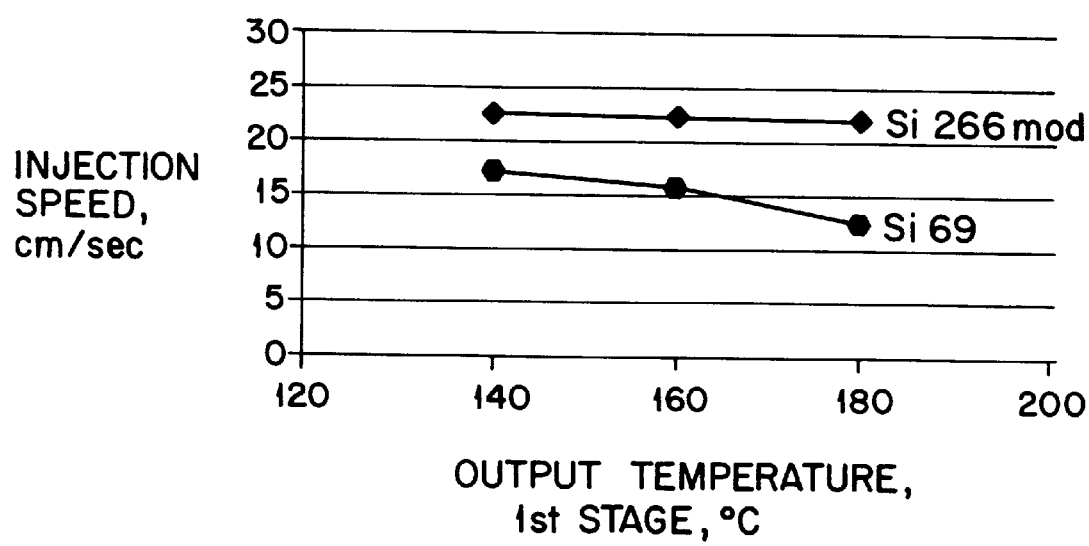

FIG. 5 shows that Si 266 mod exhibits distinct advantages in injection speed.

SPECIFIC EXAMPLES

The following examples are provided to further illustrate applicants invention.

Test Standards Used in the Examples:

| | | |
|---|---|---|
| 300% modulus | MPa | DIN 53 504 |
| Shore A hardness | — | DIN 53 505 |
| DIN abrasion | $mm^3$ | DIN 53 516 |
| MTS | | DIN 53 513 |
| Mooney viscosity | | DIN 53 523/53 524 |

The Following Chemicals are Used in the Practical Examples:

| | |
|---|---|
| Si 69 | bis(triethoxysilylpropyl)-tetrasulphane (Degussa AG). |
| Buna VSL 5025 1 HM | styrene/butadiene rubber, produced using the solution polymerisation process (Bayer AG). |
| Buna CB 11S | polybutadiene rubber (Bayer AG). |
| Naftolen ZD | aromatic plasticiser (Chemetal). |
| Vulkanox 4020 | discoloring anti-oxidant based on phenylenediamine (Bayer AG) (6PPD). |
| Protector G 35 | ozone protection wax (Fuller). |
| Vulkacit D | diphenylguanidine (Bayer AG). |
| Vulkacit CZ | benzothiazyl-2-cyclohexylsulphenamide (Bayer AG). |
| Ultrasil VN 3 GR | precipitated silica having a BET surface area of 175 $m^2/g$ (Degussa AG). |
| Si 266 | bis (triethoxysilylpropyl) disulphane. |
| Si 266 mod | in Example 3: sulphane chain distribution: 57.7% $S_2$, 31.4% $S_3$; 8.3% $S_4$; 2.3% $S_5$; 0.2% $S_6$. |

Example 1

Determination of Sulphane Chain Distribution of Various Organosilane-polysulphane Mixtures HPLC determination for the following compositions:

| Mixture % Si266/ Si69 | Weight distribution of sulphane chains | | | | | | | | | Graph point no. |
|---|---|---|---|---|---|---|---|---|---|---|
| | $S_2$ | $S_3$ | $S_4$ | $S_5$ | $S_6$ | $S_7$ | $S_8$ | $S_9$ | $S_{10}$ | |
| 100/0 | 99.7 | 0.3 | 0.0 | 0.0 | 0.0 | 0.0 | 0.0 | 0.0 | 0.0 | 1 |
| 90/10 | 83.5 | 15.3 | 1.1 | 0.0 | 0.0 | 0.0 | 0.0 | 0.0 | 0.0 | 2 |
| 80/20 | 70.2 | 25.1 | 4.1 | 0.6 | 0.0 | 0.0 | 0.0 | 0.0 | 0.0 | 3 |
| 70/30 | 57.7 | 31.4 | 8.3 | 2.3 | 0.2 | 0.0 | 0.0 | 0.0 | 0.0 | 4 |
| 60/40 | 55.7 | 22.7 | 10.2 | 6.0 | 3.1 | 1.3 | 0.6 | 0.4 | 0.1 | 5 |
| 0/100 | 16.2 | 29.9 | 24.0 | 15.2 | 7.9 | 3.8 | 2.1 | 0.6 | 0.2 | 6 |

Example 2

Determination of Scorching Using Rheometer Curve at 180° C.

All the mixtures from Example 1 were incorporated into a rubber compound according to Example 3 at approx. 140° C. using the compound formulation for stages 1 and 2, i.e. without the vulcanizing system. The minimum torque value of these unvulcanized compounds was then determined in the rheometer at 180° C. The increase in the torque value may be considered to be an indication of scorching behavior (c.f. FIG. 1).

Example 3

Comparison of Unvulcanized Compound and Rheometer Data Between Si 69 and Disulphane Mixture in a Passenger Vehicle Tread Compound

| Influence of output temperature. | | |
|---|---|---|
| Formulation | 1 | 2 |
| Buna VSL 5025 1 HM | 96 | 96 |
| Buna CB 11S | 30 | 30 |
| Ultrasil VN 3 Gr. | 80 | 80 |
| N 330 | 6.5 | 6.5 |
| Si 69 | 6.5 | — |
| Si 266 mod | — | 6.5 |
| ZnO RS | 3 | 3 |
| Stearic acid | 2 | 2 |
| Naftolen ZD | 10 | 10 |
| Vulkanox 4020 | 1.5 | 1.5 |
| Protector G35 | 1 | 1 |
| Vulkacit CZ | 1.7 | 1.7 |
| Vulkacit D | 2 | 2 |
| Sulphur | 1.4 | 2.1 |

(Si 266 mod: 57.7% $S_2$, 31.4% $S_3$, 8.3% $S_4$, 2.3% $S_5$, 0.2% $S_6$)

Compounding Instructions

Stage 1

Rotor speed: 70 rpm

Flow: 80° C.

| Compounding time | |
|---|---|
| 0–1' | Buna VSL 5025 1HM, Buna CB 11S |
| 1–2' | ½ silica, ½ Si 69 or Si 266 mod., N330, ZnO, stearic acid, oil |
| 2–3' | ½ silica, ½ Si 69 or Si 266 mod., N330, 6PPD, wax |
| 3' | clean shaft |
| 3–3.5' | mixing and discharge |
| Output temperature: 135–145° C. | |
| Intermediate storage; 24 h/RT | |

Stage 2

Rotor speed: 60 rpm

Flow: 80° C.

| Compounding time | |
|---|---|
| 0–2' | batch from stage 1 |
| 2' | discharge |
| Output temperature: 135–150° C. | |
| Intermediate storage: 24 h/RT | |

Stage 3

Rotor speed: 30 rpm

Flow: 50° C.

| Compounding time | |
|---|---|
| 0–1.5' | batch from stage 2, accelerator, sulphur |
| 1.5' | discharge |
| Output temperature: <110° C. | |

Compounding Instructions

Stage 1

Rotor speed: 95 rpm

Flow: 80° C.

| Compounding time | |
|---|---|
| 0–1' | Buna VSL 5025 1 HM, Buna CB 11S |
| 1–2' | ½ silica, ½ Si 69 or Si 266 mod., N330, ZnO, stearic acid, oil |
| 2–3' | ½ silica, ½ Si 69 or Si 266 mod., N330, 6PPD, wax |
| 3' | clean shaft |
| 3–3.5' | mixing and discharge |
| Output temperature: 155–165° C. | |
| Intermediate storage: 24 h/RT | |

Stage 2

Rotor speed: 60 rpm

Flow: 80° C.

| Compounding time | |
|---|---|
| 0–2' | batch from stage 1 |
| 2' | discharge |
| Output temperature: 135–145° C. | |
| Intermediate storage: 24 h/RT | |

Stage 3

Rotor speed: 30 rpm

Flow: 50° C.

| Compounding time | |
|---|---|
| 0–1.5' | batch from stage 2, accelerator, sulphur |
| 1.5' | discharge |
| Output temperature: <110° C. | |

Compounding Instructions

Stage 1

Rotor speed: 115 rpm

Flow: 95° C.

| Compounding time | |
|---|---|
| 0–1' | Buna VSL 5025 1HM, Buna CB 11S |
| 1–2' | ½ silica, ½ Si 69 or Si 266 mod., N330, ZnO, stearic acid, oil |
| 2–3' | ½ silica, ½ Si 69 or Si 266 mod., N330, 6PPD, wax |
| 3' | clean shaft |
| 3–3.5' | mixing and discharge |
| Output temperature: 175–185° C. | |
| Intermediate storage: 24 h/RT | |

Stage 2
Rotor speed: 60 rpm
Flow: 80° C.

| Compounding time | |
| --- | --- |
| 0–2' | batch from stage 1 |
| 2' | discharge |
| Output temperature: 135–145° C. | |
| Intermediate storage: 24 h/RT | |

Stage 3
Rotor speed: 30 rpm
Flow: 50° C.

| Compounding time | |
| --- | --- |
| 0–1.5' | batch from stage 2, accelerator, sulphur |
| 1.5' | discharge |
| Output temperature: <110° C. | |

Vulcanizate Data: 165° C./$t_{95\%}$

| | Si 69 (output temperature 140° C.) | Si 266 mod (output temperature 180° C.) |
| --- | --- | --- |
| 300% modulus MPa | 10.4 | 11.8 |
| DIN abrasion mm$^3$ | 64 | 61 |
| tan δ °C. | 0.411 | 0.473 |
| tan δ 60° C. | 0.155 | 0.160 |
| Shore A hardness | 73 | 70 |

Thanks to the elevated output temperature of 180° C. possible with Si 266 mod without any risk of scorching, the vulcanisate data obtained in this manner may be compared with those of Si 69 at an output temperature of 140° C.

Si 266 mod is distinguished by particularly good tan δ values at 0° C., which can result in improved wet skidding characteristics of the tire.

FIG. 1 shows rheometer data at 165° C. for Example 1.

FIG. 2 shows that Si 266 mod exhibits distinctly improved scorching behavior at all compounding temperatures.

FIG. 3 shows that Si 266 mod exhibits a distinctly more favorable vulcanization time in comparison with Si 69.

For unvulcanized compound data, FIG. 4 shows that even at elevated compounding temperatures, Si 266 mod exhibits no scorching and thus has distinctly better processing behavior.

FIG. 5 shows that Si 266 mod exhibits distinct advantages in injection speed.

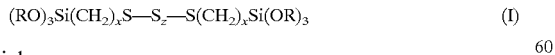

What is claimed is:

1. A composition comprising a mixture of organosilane-polysulphanes of the general formula $$(RO)_3Si(CH_2)_xS—S_z—S(CH_2)_xSi(OR)_3 \quad (I)$$

in which
R is a linear or branched alkyl, having 1–8 carbon atoms,
x is an integer from 1–8, and
z is 0 to 6,
wherein
the proportion of polysulphanes in which z is an integer from 2 to 6 is greater than 0 wt. % and does not exceed a proportion of 20 wt. % based on the total amount of the mixture of polysulphanes, and at least one polysulphane defined by z=5 or z=6 is present in the polysulphane mixture, and
the proportion of polysulphanes where z=0 is less than 80 wt. % based on the total amount of the mixture of polysulphanes, and the sum of the proportions of said polysulphanes in which z=0 and z=1 is ≧80 wt. %.

2. A vulcanizable composition resistant to scorching at elevated vulcanization temperatures comprising a vulcanization rubber, a vulcanization agent, vulcanization auxiliaries, a filler, and 0.5 to 30 wt. parts per 100 wt. parts filler of a mixture of organosilanepolysulphanes according to claim 1.

3. A vulcanizable composition according to claim 2 comprising, per 100 weight parts rubber, 0.1 to 4 wt. parts of a sulfur and/or sulfur donor vulcanization agent and 10–200 wt. parts of a silica filler.

4. A shaped vulcanized rubber product comprising the vulcanizable composition of claim 2.

5. A shaped vulcanized rubber product comprising the vulcanizable composition of claim 3.

6. A rubber tire tread which comprises the vulcanized rubber product of claim 4.

7. A rubber tire tread which comprises the vulcanized rubber product of claim 5.

8. A process for the production of sulfur vulcanized rubber compounds which comprises the steps of
(1) mixing together a vulcanizable rubber compound, a mixture of organosilanepolysulphanes according to claim 1, a silicate filler optionally together with carbon black,
(2) kneading mixture formed in step (1) at a temperature of 16° to 200° C. until a uniform mixture is obtained,
(3) subjecting the uniform mixture obtained in step (2) to further mixing at a temperature in the range of 60° C. to 120° C. and adding vulcanization auxiliaries during mixing and continuing mixing at 60° C. to 120° C. until a vulcanized rubber product is obtained, and
(4) rolling the vulcanized rubber product thus obtained into sheets or strips.

9. The process according to claim 8 wherein the silicate filler is a light colored oxide filler selected from the group consisting of natural fillers, precipitated silica, silicates, and mixtures thereof, and is present in an amount ranging from 10 to 200 weight parts per 100 weight parts of rubber (phr).

10. The process according to claim 8 wherein the filler has a BET surface area of 1 to 700 m2/g.

11. The process according to claim 9 wherein the precipitated silicas and silicates have a DBP value of 150 to 300 ml/100 g.

12. The process according to claim 8 wherein 0.5 to 30 parts of a mixture of organosilanepolysulphanes per 100 parts of filler is present in step (1).

13. The composition according to claim 1, comprising a mixture of organosilanepolysulphanes of formula (I), wherein said mixture comprises:
an organosilanepolysulfane, wherein z=0, in an amount from 58 wt. % to <80 wt. %;
an organosilanepolysulfane, wherein z=1, in an amount from greater than 0 wt. % to 32 wt. %, wherein the sum of the wt. % for z=0 and z=1 is ≧80 wt. %; and one or more organosilanepolysulphanes, wherein z=2 to 6, in a combined amount of greater than 0 wt. % and ≦20 wt. % for the remainder of the mixture of organosilanepolysulphanes and at least one polysulphane defined by z=5 or z=6 is present in the mixture.